(12) United States Patent
Yazicioglu et al.

(10) Patent No.: US 8,454,505 B2
(45) Date of Patent: Jun. 4, 2013

(54) METHOD AND ELECTRONIC MEDICAL DEVICE FOR SIMULTANEOUSLY MEASURING AN IMPEDANCE AND A BIOPOTENTIAL SIGNAL

(75) Inventors: Refet Firat Yazicioglu, Leuven (BE); Sunyoung Kim, Leuven (BE)

(73) Assignee: IMEC, Leuven (BE)

( * ) Notice: Subject to any disclaimer, the term of this patent is extended or adjusted under 35 U.S.C. 154(b) by 86 days.

(21) Appl. No.: 12/882,126

(22) Filed: Sep. 14, 2010

(65) Prior Publication Data
US 2011/0066054 A1 Mar. 17, 2011

Related U.S. Application Data

(60) Provisional application No. 61/242,299, filed on Sep. 14, 2009.

(30) Foreign Application Priority Data

Feb. 1, 2010 (EP) ..................................... 10152299

(51) Int. Cl.
*A61B 5/00* (2006.01)
(52) U.S. Cl.
USPC ........................................................ 600/300
(58) Field of Classification Search
USPC .......................................... 600/300, 508, 509
See application file for complete search history.

(56) References Cited

U.S. PATENT DOCUMENTS

| | | | |
|---|---|---|---|
| 3,667,056 A | 5/1972 | Allington et al. | |
| 4,610,254 A | 9/1986 | Morgan et al. | |
| 4,669,301 A | 6/1987 | Kratt et al. | |
| 5,020,541 A | 6/1991 | Marriott | |
| 5,197,479 A * | 3/1993 | Hubelbank et al. | 600/508 |

(Continued)

FOREIGN PATENT DOCUMENTS

| | | |
|---|---|---|
| EP | 0540144 | 5/1993 |
| EP | 0884851 | 12/1998 |

(Continued)

OTHER PUBLICATIONS

R.F. Yazicioglu et al., "Ultra-Low-Power Wearable Biopotential Sensor Nodes", .31$^{st}$ Annual International Conference of the IEEE EMBS Minneapolis, Minnesota, USA, pp. 3205-3208, Sep. 2-6, 2009.

(Continued)

*Primary Examiner* — Brian T Gedeon
(74) *Attorney, Agent, or Firm* — Knobbe Martens Olson & Bear LLP (57) ABSTRACT

A method and device is disclosed for continuously and simultaneously measuring an impedance signal and a biopotential signal on a biological subject's skin. In one aspect, the method includes attaching input and output electrodes to the biological subject's skin and applying a predetermined alternating current having a first frequency to the output electrodes for creating an alternating voltage signal over the input electrodes. The first frequency is above a predetermined minimum frequency. The method also includes measuring an input signal from the input electrodes which includes a biopotential signal and the alternating voltage signal. The method also includes extracting from the input signal the biopotential signal and the alternating voltage signal, and determining the impedance signal from the alternating voltage signal. The alternating voltage signal is extracted by amplifying and demodulating the input signal using a control signal having a frequency equal to the first frequency.

11 Claims, 8 Drawing Sheets

U.S. PATENT DOCUMENTS

| | | | |
|---|---|---|---|
| 5,381,803 | A | 1/1995 | Herleikson et al. |
| 6,714,813 | B2 * | 3/2004 | Ishigooka et al. ............ 600/547 |
| 6,821,254 | B2 * | 11/2004 | Weil et al. ...................... 600/484 |
| 8,068,905 | B2 * | 11/2011 | Freeman et al. ............... 600/547 |
| 2003/0006782 | A1 | 1/2003 | Shambroom et al. |
| 2007/0060802 | A1 | 3/2007 | Ghevondian et al. |
| 2008/0183098 | A1 | 7/2008 | Denison et al. |
| 2010/0324404 | A1 * | 12/2010 | Harrold et al. ................ 600/391 |

FOREIGN PATENT DOCUMENTS

| | | |
|---|---|---|
| EP | 1754441 A1 | 2/2007 |
| EP | 2086111 | 8/2009 |
| WO | WO 2004/052198 A1 | 6/2004 |
| WO | WO 2008/073528 A1 | 6/2008 |

OTHER PUBLICATIONS

R.F. Yazicioglu et al., "A 200 µW Eight-Channel EEG Acquisition ASIC for Ambulatory EEG Systems", IEEE Journal of Solid-State Circuits, vol. 43, No. 12, pp. 3025-3038, Dec. 2008.

A.-T. Avestruz et al,. "A 5 µW/Channel Spectral Analysis IC for Chronic Bidirectional Brain-Machine Interfaces", IEEE Journal of Solid-State Circuits, vol. 43, No. 12, pp. 3006-3024, Dec. 2008.

C.C. Enz et al., "Circuit Techniques for Reducing the Effects of Opamp Imperfections", Proc. of IEEE, vol. 84, No. 11, pp. 1584-1614, Nov. 1996.

R.R. Harrison et al., "A Low-Power Low-Noise CMOS Amplifier for Neural Recording Applications", IEEE J. Solid State Circuits, vol. 38, No. 6, pp. 958-965, Jun. 2003.

J. Ottenbacher et al., "Reliable Motion Artifact Detection for ECG Monitoring Systems with Dry Electrodes", IEEE EMBS Conf., pp. 1695-1698, Aug. 2008.

X.D. Zou et al., "A 1V 450nW Fully Integrated Programmable Biomedical Sensor Interface System", IEEE J. of Solid-State Circuits, vol. 44, No. 4, pp. 1067-1077, Apr. 2009.

ANSI/AAMI-EC13, "American national standards for cardiac monitors, hearth rate meters and alarms", Association for the Advancement of Medical Instrumentation, 2002.

B. Gyselinckx et al., "Human++: Energing Technology for Body Area Networks", Very Large Scale Integration, 2006 IFIP International Conference, pp. 175-180, Oct. 2006.

J. Penders et al., "Human++: from Technology to Emerging Health Monitorning Concepts", Proceedings of the 5th International Workshop on Wearable and Implantable Body Sensor Networks, pp. 94-98, Jun. 1-3, 2008.

R.F. Yazicioglu et al., "A 60µW 60nVh/√Hz Readout Front-end for Portable Biopotential Acquisition Systems", IEEE J. Solid-State Circuits, vol. 42, No. 5, pp. 110-1110, May 2007.

C Enz., "A CMOS Chopper Amplifier", IEEE J. Solid-State Circuits, vol. 22, No, 3, pp. 335-342, Jun. 1987.

MSJ Steyaert et al., "A Micropower Low-Noise Monolithic Instrumentation Amplifier for Medical Purposes", IEEE J. Solid-State Circuits, vol. sc-22, No. 6, lines 1163 to 1168, Dec. 1987.

I Romero et al., "Low-Power Robust Beat Detection in Ambulatory Cardiac Monitoring", IEEE BioCAS, pp. 249-252, Nov. 2009.

H. Tam et al., "Minimizing Electrode Motion Artifact by Skin Abrasion", IEEE Trans. on Biomedical Engineering, vol. BME-24, pp. 134-139, 1977.

M Trakimas et al., "A 0.8V Asynchronous ADC for Energy Constrained Sensing Application", IEEE CICC, pp. 173-176, Sep. 2008.

Jalaleddine et al., "ECG data compression techniques—A unified approach", IEEE trans on Biomed. Eng., vol. 37, No. 4, Apr. 1990.

Kalinin et al., "A simple method to adapt time sampling of the analog signal", Nuclear Instruments and Methods in Physics Research A 524 (2004), pp. 374-376.

H. Kim et al., "A Low Cost Quadratic Level ECG Compression Algorithm and Its Hardware Optimization for Body Sensor Network System", IEEE EMBS 2008, pp. 5490-5493, Aug. 2008.

Extended European Search Report for European Patent Application No. 10176687.1-1265 dated Nov. 21, 2011.

Bohs L N et al., "Real-time adaptive sampling with the fan algorithm", Medical and Biological Engineering and Computing, Springer, Heildelberg, DE, vol. 26, No. 6, Nov. 1, 1988, pp. 563-573.

Barr et al., "Adaptive sampling of cardiac waveforms", Journal of Electrocardiology, Elsevier Science, vol. 21, Jan. 1, 1988, pp. S57-S60.

Rieger R et al., "An Adaptive Sampling System for Sensor Nodes in Body Area Networks", IEEE Transactions of Neural Systems and Rehabilitation Engineering, IEEE Service Center, New York, NY, US, vol. 17, No. 2, Apr. 1, 2009, pp. 183-189.

Bohs L N et al., "Prototype for real-time adaptive sampling using the fan algorithm", Medical and Biological Engineering and Computing, Springer, Heildelberg, DE, vol. 26, No. 6, Nov. 1, 1988, pp. 574-583.

Rieger R. et al., "A Signal Based Clocking Scheme for A/D Converters in Body Sensor Networks", Tencon 2006. 2006 IEEE Region 10 Conference, IEEE, PI, Nov. 14, 2006, pp. 1-4.

Extended European search report for European Patent Application No. 10176639.2 -1265 dated Dec. 23, 2010 by European Patent Office.

* cited by examiner

METHOD AND ELECTRONIC MEDICAL DEVICE FOR SIMULTANEOUSLY MEASURING AN IMPEDANCE AND A BIOPOTENTIAL SIGNAL

CROSS REFERENCE TO RELATED APPLICATIONS

This application claims priority under 35 U.S.C. §119(e) to U.S. provisional patent application 61/242,299 filed on Sep. 14, 2009. This application is related to U.S. application Ser. No. 12/882,118, filed on the same day herewith and titled "ADAPTIVE SAMPLING," and U.S. application Ser. No. 12/882,120, filed on the same day herewith and titled "ANALOGUE SIGNAL PROCESSORS." Each of the above applications is hereby incorporated by reference in its entirety.

BACKGROUND OF THE INVENTION

1. Field of the Invention

The present invention relates to a method for continuously and simultaneously measuring an impedance and a biopotential signal on a biological subject.

The invention also relates to an electronic medical device for continuously and simultaneously measuring an impedance and a biopotential signal on a biological subject.

The invention also relates to the use of such an electronic medical device for measuring a biopotential signal (Electrocardiogram (ECG), Electroencephalogram (EEG), Electromyogram (EMG), etc.).

2. Description of the Related Technology

Several readout circuits for ambulatory monitoring of biopotential signals have been proposed in the prior art. For battery powered portable devices that are continuously monitoring electronic signals, power efficiency is of primary importance to guarantee sufficient autonomy.

In addition, field tests have revealed that motion artifacts are a significant problem for accurate and robust signal acquisition, in order to differentiate between biological information and unwanted motion artifacts. Movement artifacts are the biggest source of noise in mobile ECG recordings. These artifacts are potentials that are superimposed onto the ECG signal. These potentials occur in the electrode cables, in the skin and at the electrode/electrolyte interface. While artifacts coming from cables can be reduced by appropriate electrode cables, artifacts from the skin and electrode/electrolyte interface are difficult to reduce by design.

Figure 2:
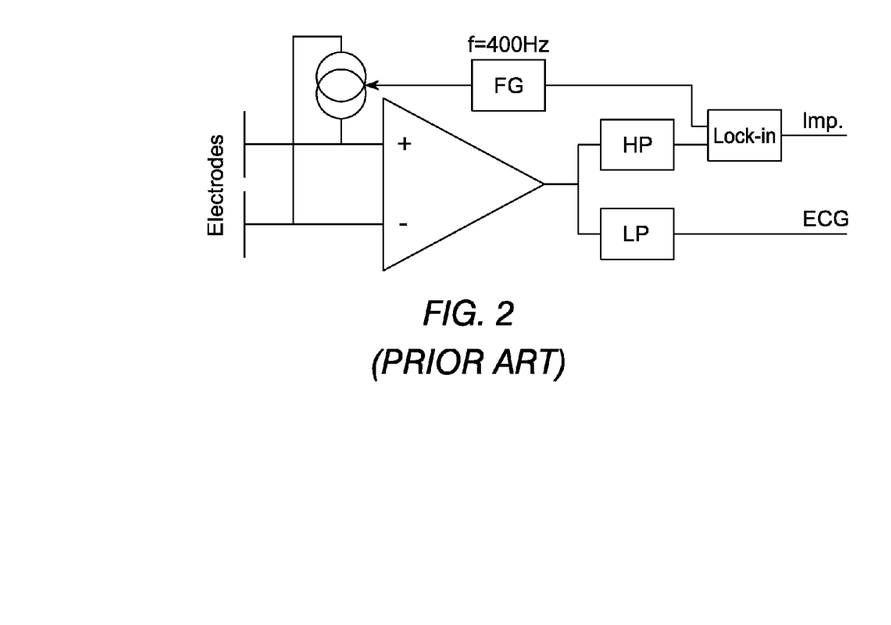
FIG. 2 shows a block diagram of a prior art circuit for injecting an alternating current and measuring an alternating voltage.

R. F. Yazicioglu et al. have described in "Ultra-Low-Power Wearable Biopotential Sensor Nodes," IEEE EMBS conf., September 2009, a circuit (see FIG. 2) that injects an AC current and measures the voltage generated across the electrode impedance to continuously monitor the electrode impedance. The AC current frequency is selected to be large enough compared to the biopotential signals so that selective filtering at the backend can be used to differentiate between the biopotential signal and the voltage generated due to the electrode impedance. A disadvantage of the disclosed approach is that it requires the use of sinusoidal current sources and analog multipliers and also it requires a high sampling rate in the subsequent analog to digital conversion step (ADC), where both leads to high power consumption.

US 2008/0183098 A1 describes a chopper stabilized instrumentation amplifier for measuring different types of physiological information captured by means of an implantable pulse generator implanted in a patient.

SUMMARY OF CERTAIN INVENTIVE ASPECTS

Certain inventive aspects relate to a method and device for measuring a biopotential signal together with an impedance signal on a subject's skin, with which a reduced power consumption can be achieved.

One inventive aspect relates to a method and device for continuously and simultaneously measuring an impedance signal and a biopotential signal on a biological subject's skin, the method comprising the steps of: attaching input and output electrodes to the biological subject's skin; applying a predetermined alternating current having a first frequency to the output electrodes for creating an alternating voltage signal over the input electrodes, the first frequency being above a predetermined minimum frequency; measuring an input signal from the input electrodes, the input signal comprising a biopotential signal and the alternating voltage signal; extracting from the input signal the biopotential signal; extracting from the input signal the alternating voltage signal and determining the impedance signal from the alternating voltage signal. The alternating voltage signal is extracted by amplifying and demodulating the input signal using a control signal having a frequency equal to the first frequency of the applied alternating current.

In one aspect, the electronic medical device comprises: input and output electrodes provided for being attached to the biological subject's skin and connected to input and output terminals of the device; a current source connected to the output terminals, for generating a predetermined alternating current having a first frequency above a predetermined minimum frequency which is applied to the output electrodes for creating an alternating voltage signal over the input electrodes; an impedance signal extraction block, connected to the input terminals, for extracting the alternating voltage signal from an input signal which is measured on the input electrodes and determining the impedance signal from the alternating voltage signal; a biopotential signal extraction block, connected to the input terminals, for extracting the biopotential signal from the input signal. The impedance signal extraction block comprises a first amplifier connected to the input terminals for amplifying the input signal and a demodulation block connected to the first amplifier for demodulating the input signal using a control signal having a frequency equal to the first frequency.

In one inventive aspect, the first frequency of the predetermined alternating current is chosen in function of the biopotential signal which is measured. In particular, the first frequency is selected to be sufficiently different from that of the biopotential signal to facilitate differentiation between the biopotential signal and the alternating voltage signal (which results from the current), which are simultaneously captured in the input signal. The biopotential signal, being a baseband signal, can for example be extracted using a low pass filter (LPF) made of passive components, which is a low power solution. The effect of demodulating the alternating voltage with the control signal at the first frequency is that the alternating voltage signal is demodulated to baseband while the biopotential signal is upconverted with the first frequency. As a result, also the alternating voltage signal can be extracted using a low pass filter (LPF) made of passive components, instead of the active bandpass filter (BPF) requiring active power which was used in the prior art. Because both signals are baseband signals additional power can be saved in the further processing stages, such as an analog to digital (ADC) stage which can run at a much lower frequency as compared to a direct digitization of the alternating voltage at the first frequency.

In certain embodiments, the extraction of the alternating voltage signal comprises extracting in parallel a first and a second baseband voltage signal representative of real and imaginary components of the impedance signal. This means that the first and second baseband voltage signals are obtained by demodulating the input signal using two control signals having a frequency equal to the first frequency but 90° phase shifted with respect to each other. By demodulating the alternating voltage in this way, the amplitude of the impedance can be accurately determined even during motion of the biological subject. This impedance can then be used in subsequent processing stages to detect and/or to compensate motion artifacts. Since both impedance signals and the biopotential signal are baseband signals, all three signals can be sampled at a low sampling rate. Lowering the impedance measurement frequency is advantageous in terms of evaluating the imaginary part of the electrode impedance (the lower the frequency, the higher SNR can be achieved). Furthermore, the use of current mode measurement has minimal effect on the input impedance of the amplifier which enables the precise measurement of the electrode impedance including the real (resistive) and the imaginary (capacitive) part.

In certain embodiments, the predetermined alternating current is generated by chopper modulating a predetermined DC current using the first control signal, and the demodulations of the input signal for extracting the first and second baseband impedance signals is a chopper demodulation controlled by control signals at the same first frequency. Chopper modulation is a power efficient solution for modulating analog signals and shifts their frequency spectrum to desired locations. The proposed solution uses chopper modulation to efficiently separate the frequency bands of the impedance measurement signal (the alternating voltage) and the biopotential signal. Furthermore, the use of chopper modulation and demodulation eliminates the requirement for bandpass filters (BPF), which can be very power consuming if higher order BPF is required, instead only low-pass filters can be used, which can be implemented using only passive components.

Additionally chopper modulation and demodulation can suppress DC-offset and low frequency noise introduced by the amplifier circuitry.

In certain embodiments, the biopotential signal is extracted from the input signal by subsequent chopper modulation, amplification and chopper demodulation of the input signal, whereby again the first frequency is used.

Converting the biopotential signal back to a baseband signal is good for power savings for the same reasons as described above (low pass filter and lower ADC rate).

In addition, by requiring only a single clock frequency, all clock signals can be derived from a single clock source, saving circuitry and allowing a higher timing accuracy and further power savings.

In one aspect, the method and device can for example be used for measuring one of the following biopotential signals: ECG, EEG, EMG or other. The impedance signal can be used for detecting motion artifacts within biopotential signals or removing motion artifacts from the biopotential signal.

BRIEF DESCRIPTION OF THE DRAWINGS

The invention will be further elucidated by means of the following description and the appended drawings, wherein like reference numerals refer to like elements in the various drawings. The drawings described are only schematic and the invention is not limited thereto. In the drawings, the size of some of the elements may be exaggerated and not drawn on scale for illustrative purposes.

DETAILED DESCRIPTION OF CERTAIN ILLUSTRATIVE EMBODIMENTS

An important noise source for ambulatory monitoring systems is the motion/movement artifact. Since the subject/patient is continuously moving, the relative movement of the electrode with respect to human skin/tissue results in a significant change in the half-cell potential of the electrode-tissue interface. This converts to a voltage value which can have a larger amplitude than the biopotential signals. In addition, these artifacts may have similar frequency spectrum as the biopotential signals. Hence, both the amplitude based and the frequency based biomedical signal analysis algorithms can significantly suffer from these motion artifacts.

In the embodiments described below, a continuous impedance measurement is performed as an approach to detect or to reduce the motion artifacts. The impedance measurement can be implemented in a low power fashion and without an additional sensor. It will become clear from the description how the biopotential measurement and the impedance measurement can be performed simultaneously and in a continuous way without affecting the signal quality of the biopotential signal measurement. Note that in alternative embodiments, the same impedance measurement can also be used to extract other information, such as for example respiration of a patient.

The embodiments described below provide a method and an electronic medical device for a power-efficient acquisition of a biopotential signal such as an ECG signal, with reduced motion artifacts. The proposed method uses a continuous-time electrode-tissue impedance monitoring for sensing the presence of motion artifacts.

The proposed solution is suitable for measuring a variety of biopotential signals, such as e.g. ECG or EEG signals or other biopotential signals, and will be described in further detail for ECG signals as one example of a biopotential signal, without limiting the invention thereto.

Figure 1:
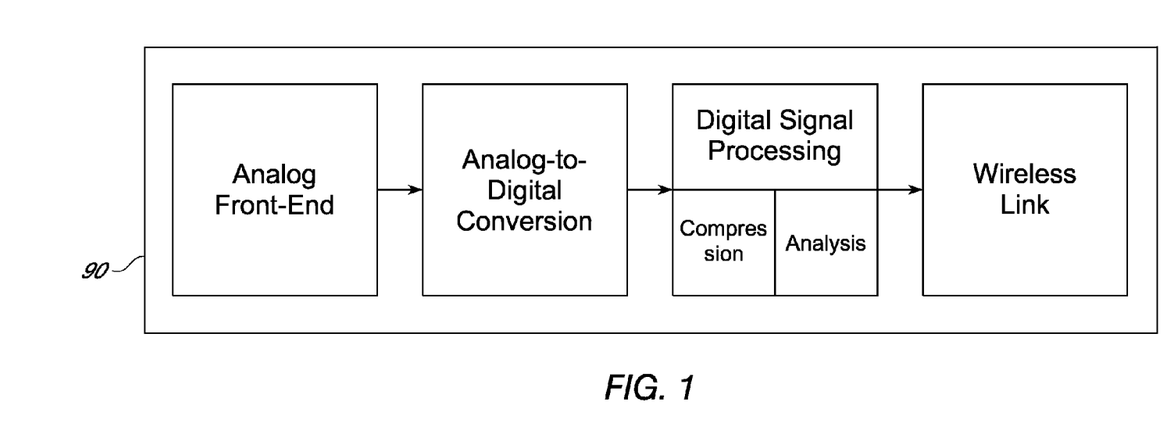
FIG. 1 shows a typical block diagram of an electronic medical device, in particular a wireless biomedical device.

FIG. 1 shows a block diagram of an example of a portable biomedical device (90) for processing biopotential signals, e.g. electrocardiogram (ECG) signals. After the ECG signal is extracted using the analog-readout front-end, it is digitized using an analog to digital conversion (ADC) block. The output of the ADC block is processed by a digital signal processor (DSP), this can include compression of the signal and feature extraction, after which the output data is sent through the wireless link. The main focus of the description below is the signal acquisition of the analog front end. An additional power improvement can be achieved in the ADC block, as will be described further.

Figure 3:
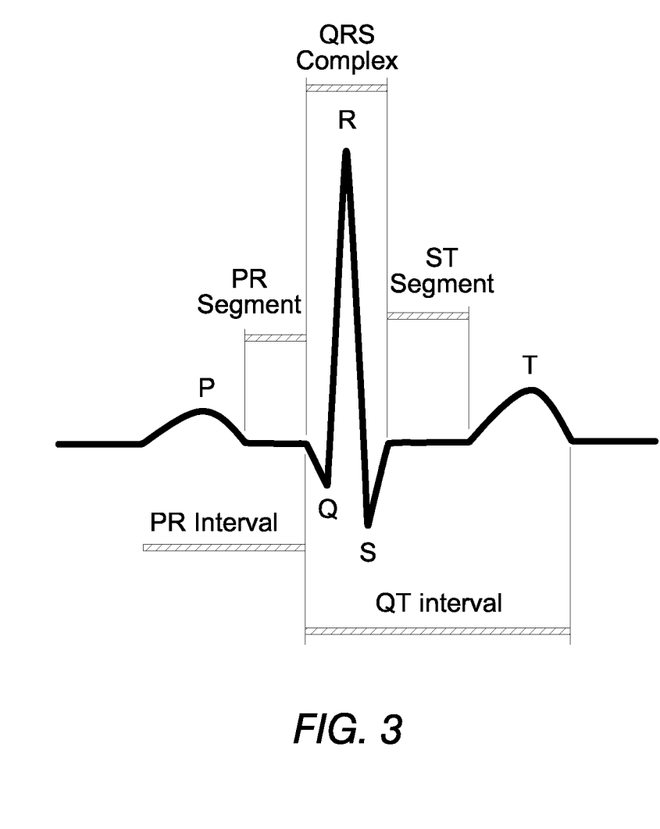
FIG. 3 shows a typical ECG signal.

A typical ECG signal to be measured is shown in FIG. 3. It consists of a P wave, a QRS complex and a T wave. Among these three signals, the QRS complex has the highest frequency, while the rest of the signal has low frequencies. The ECG signal has a frequency spectrum typically located between 0.1 Hz and 250 Hz. As used herein, 250 Hz is the "expected maximum frequency" of a typical ECG signal. Other biopotential signals may however have another expected maximum frequency.

Figure 4:
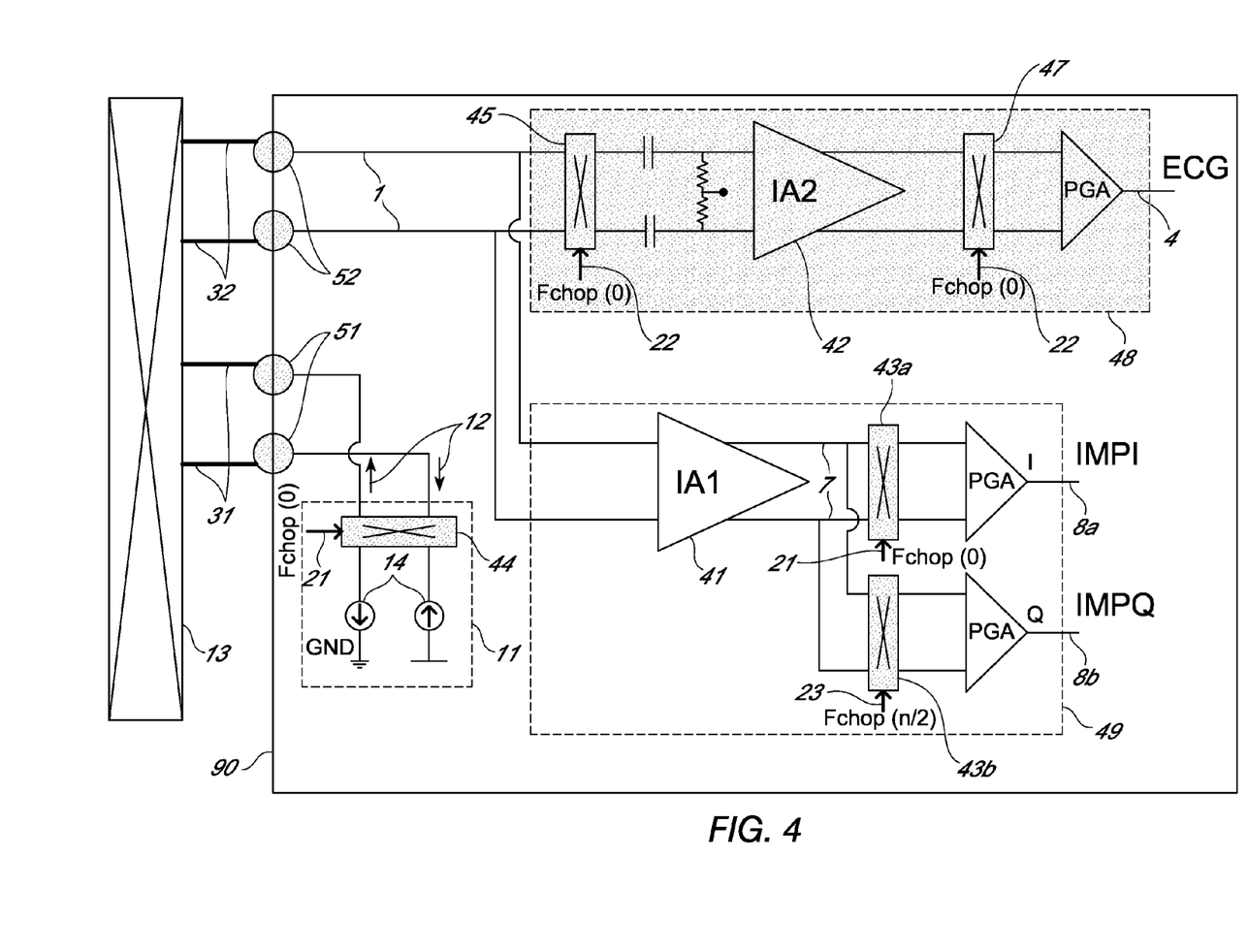
FIG. 4 shows a block diagram of an analog front end of an electronic medical device according to one embodiment.

FIG. 4 shows a block-diagram of part of an electronic medical device 90 for continuously and simultaneously measuring an impedance and a biopotential signal 4 on the skin of a biological subject 13. It comprises a current source 11 for generating a predetermined alternating current 12 having a first frequency, output terminals 51 for applying the alternating current 12 to electrodes 31 on the skin 13 for creating an alternating voltage signal, input terminals 52 for measuring an input signal 1 from electrodes 32 on the skin 13, an impedance signal extraction block 49 for extracting an impedance signal 8 from the input signal 1, and a biopotential signal extraction block 48 for extracting a biopotential signal 4 from the input signal 1. The impedance signal extraction block 49 comprises a first instrumentation amplifier 41 connected to a first and second demodulator 43a, 43b for extracting a first and a second baseband impedance signal 8a, 8b, the first resp. second demodulator 43a, 43b using a first resp. third control signal 21, 23 both having a frequency equal to the first frequency. The third control signal 23 is 90° phase shifted with respect to the first control signal 21. In this way, real and imaginary parts of the impedance signal are demodulated simultaneously.

The first frequency is chosen above a predetermined minimum, which is selected for achieving spectral separation of the biopotential and impedance signals. The first frequency is preferably at least twice the expected maximum biopotential frequency, i.e. preferably at least 500 Hz for ECG.

From the known (predetermined) current and the measured alternating voltage an impedance can then be derived. The electrodes 31 and 32 are placed on the skin. The measured impedance is from the input signal measured by means of the electrodes 32 is the impedance of the biological skin tissue between the electrodes. The impedance can be a complex value, having a real and an imaginary part, especially when the electrodes 31, 32 are moving.

Using an alternating current 12 prevents corrosion of the electrodes. The current is typically chosen smaller than 1 µA, or preferably even smaller than 100 nA, so that the alternating voltage amplitude is limited, e.g. to the same order of magnitude as the biopotential signal.

As the maximum frequency of an ECG signal typically is 250 Hz, the first frequency for measuring an ECG signal is e.g. 500 Hz, but the invention will also work for higher or lower frequencies. The alternating current 12 can e.g. be a sine wave or a square wave, or any other waveform found suitable by the person skilled in the art.

The first amplifier is preferably an instrumentation amplifier 41, meaning an amplifier that implements a certain predefined multiplication for the input signal.

In order to measure the complex impedance value, two impedance signals 8a, 8b with a 90° phase shift are continuously extracted, so that an impedance amplitude can be calculated on a continuous basis.

Depending on the modulation and demodulation technique, the control signals 21, 23 can e.g. be sine waves or clock signals, or other signals.

The current source 11 comprises a DC current generator 14 and a first chopper modulator 44 controlled by a first control signal 21 for generating the predetermined alternating current 12. The first and second demodulators 43a, 43b are chopper demodulators controlled by the first resp. third control signal 21, 23. Chopper modulation of a differential incoming signal can e.g. be implemented by a double switch which is either directly or inversely coupled to a differential output, whereby the control signal controls the state of the switch. For chopper modulation, the control signals typically are clock signals with a 50% duty cycle.

The biopotential signal extraction block 48 comprises a second chopper modulator 45 connected to a second instrumentation amplifier 42, connected to a second chopper demodulator 47, both the modulator 45 and demodulator 47 being controlled by a second clock signal 22 having a second frequency, whereby the second frequency is the same as the first frequency. Chopper stabilization of the second instrumentation amplifier 42 offers the advantage of cancelling DC offset and reducing low frequency noise introduced by the second instrumentation amplifier 42. Optionally the chopper demodulator is followed by a programmable gain amplifier (PGA) before entering an ADC for matching the signal amplitude to the subsequent ADC input range.

Figure 5:
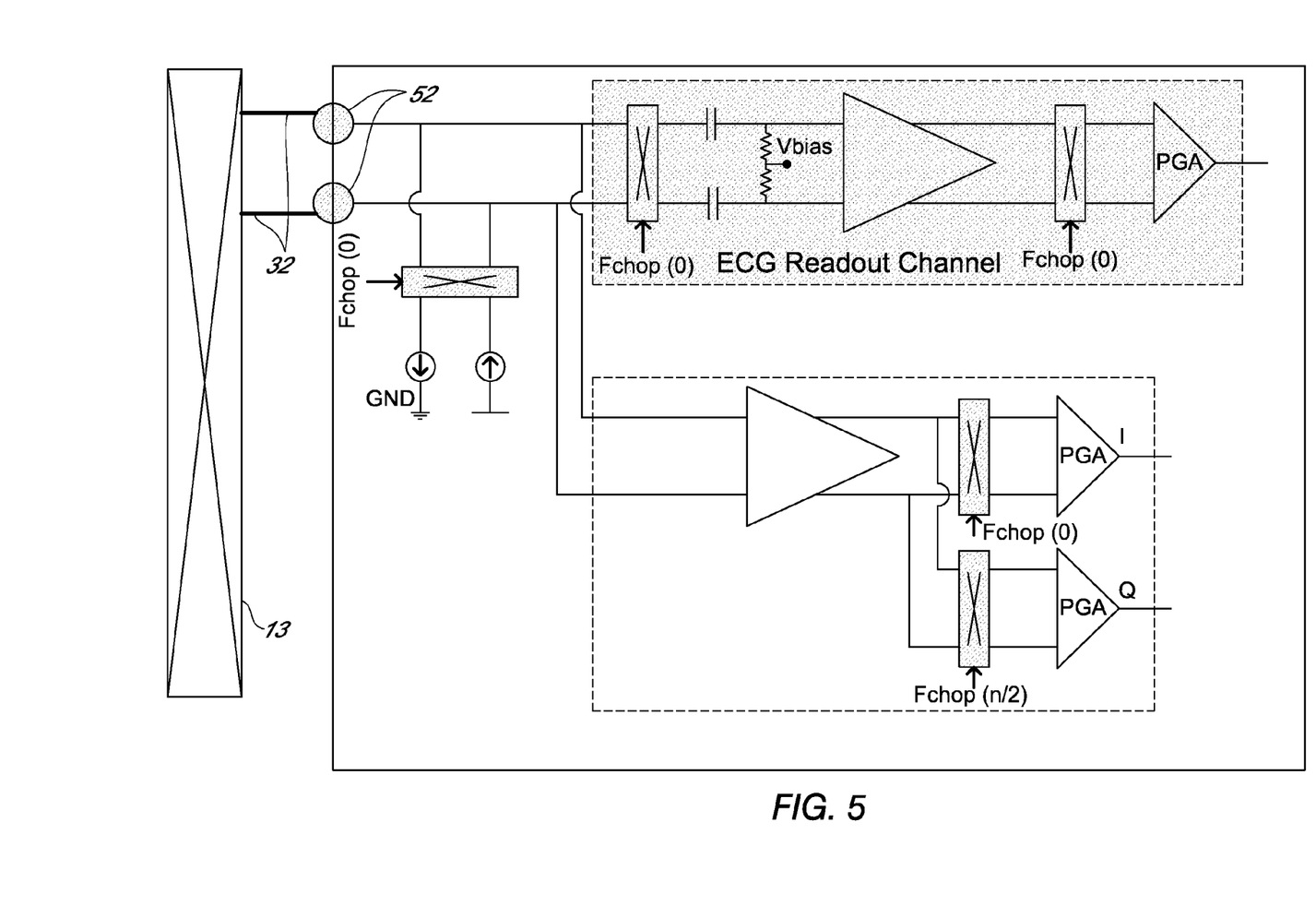
FIG. 5 shows a variant of FIG. 4, using a single set of electrodes.

In FIG. 4 the terminals 52 and electrodes 32 for measuring the input signal 1 and the terminals 51 and electrodes 31 for applying the alternating current 12 are different terminals and electrodes. Other topologies are possible however, e.g. a single set of terminals 51 and electrodes 31 could be used, as shown in FIG. 5. By using a single set of electrodes 32, movement artefact signals show a maximum correlation to both the impedance 8a, 8b and the biopotential signal 4. A single set of electrodes is also preferred by a patient.

In the case of FIG. 5, the impedance which is derived from the known (predetermined) current and the measured alternating voltage is the impedance of the electrodes 32, the impedance of the biological skin tissue between the electrodes 32 and the half-cell potential of the electrode-tissue interface. The impedance can be a complex value, having a real and an imaginary part, especially when the electrodes 32 are moving.

Figure 6:
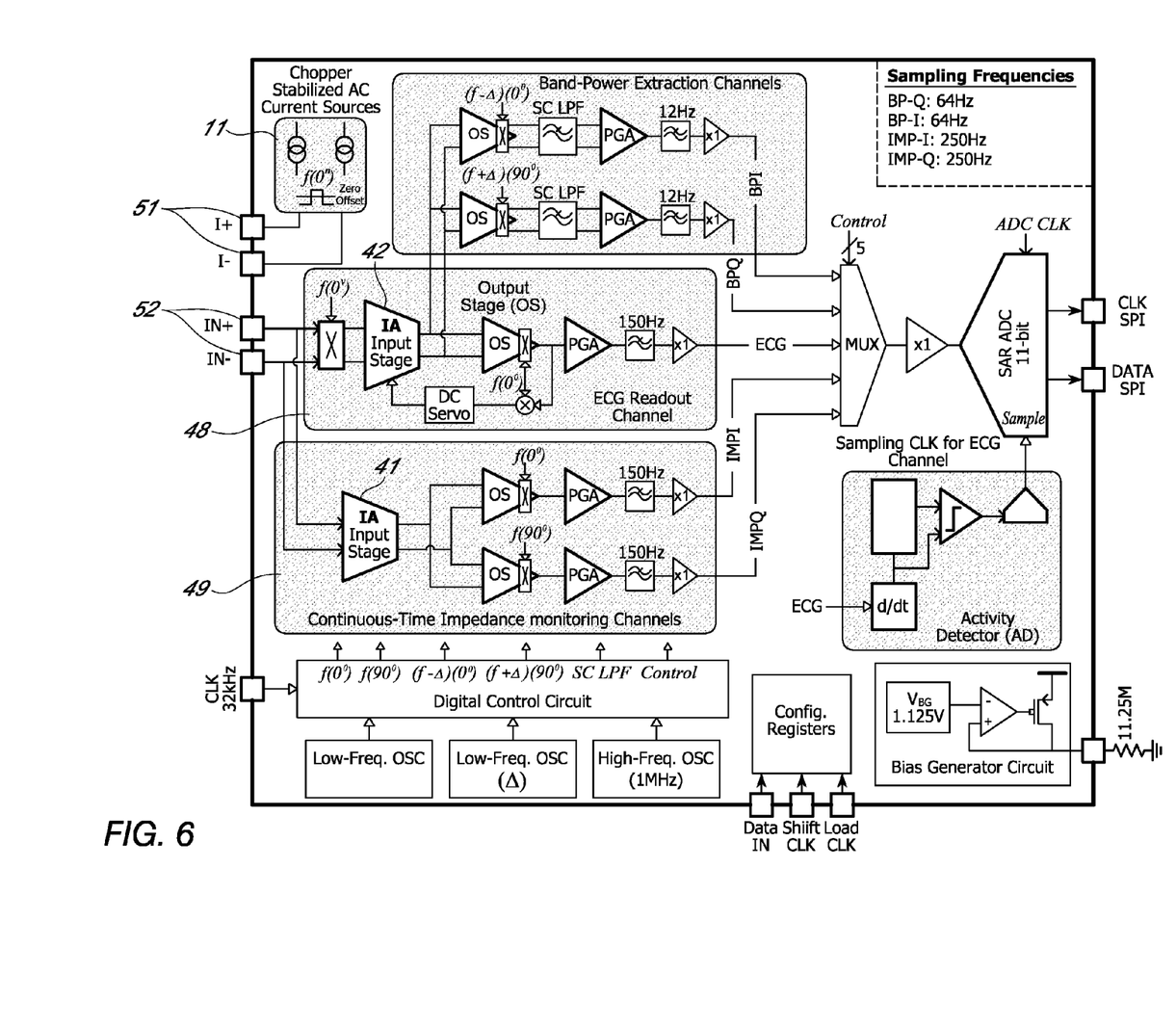
FIG. 6 shows an example of an Analog Signal Processor ASIC (ASP) architecture according to one embodiment.

In FIG. 6 an embodiment of a signal processor is illustrated. The analog signal processor (ASP) comprises an ECG readout channel, two quadrature readout channels for continuous-time (CT) monitoring of electrode-tissue impedance, two quadrature readout channels for tracking power fluctuations in a specific frequency band, and an activity detector (AD) that can sense the frequency content (e.g. by determining the slope) of the ECG signal and comprises a SAR (successive approximation)-ADC. The ECG readout channel of the ASP uses a chopper stabilized instrumentation amplifier (IA) architecture for increasing common mode rejection ratio (CMRR) and reducing flicker noise (also called 1/f noise). This or a similar circuit can also be used for other biopotential signal measurements, not only for ECG signals.

Optionally the current source 11 has means for adjusting the polarity of the modulated current 12 for measuring either a total impedance or an impedance difference.

By adjusting the polarity of the currents 12, either the total impedance or the impedance difference between two electrodes can be characterized. The prior can be attractive for measuring the actual impedance of the electrodes for the continuous time electrode quality assessment, and the latter can be used to monitoring motion/movement artifacts.

Figure 7:
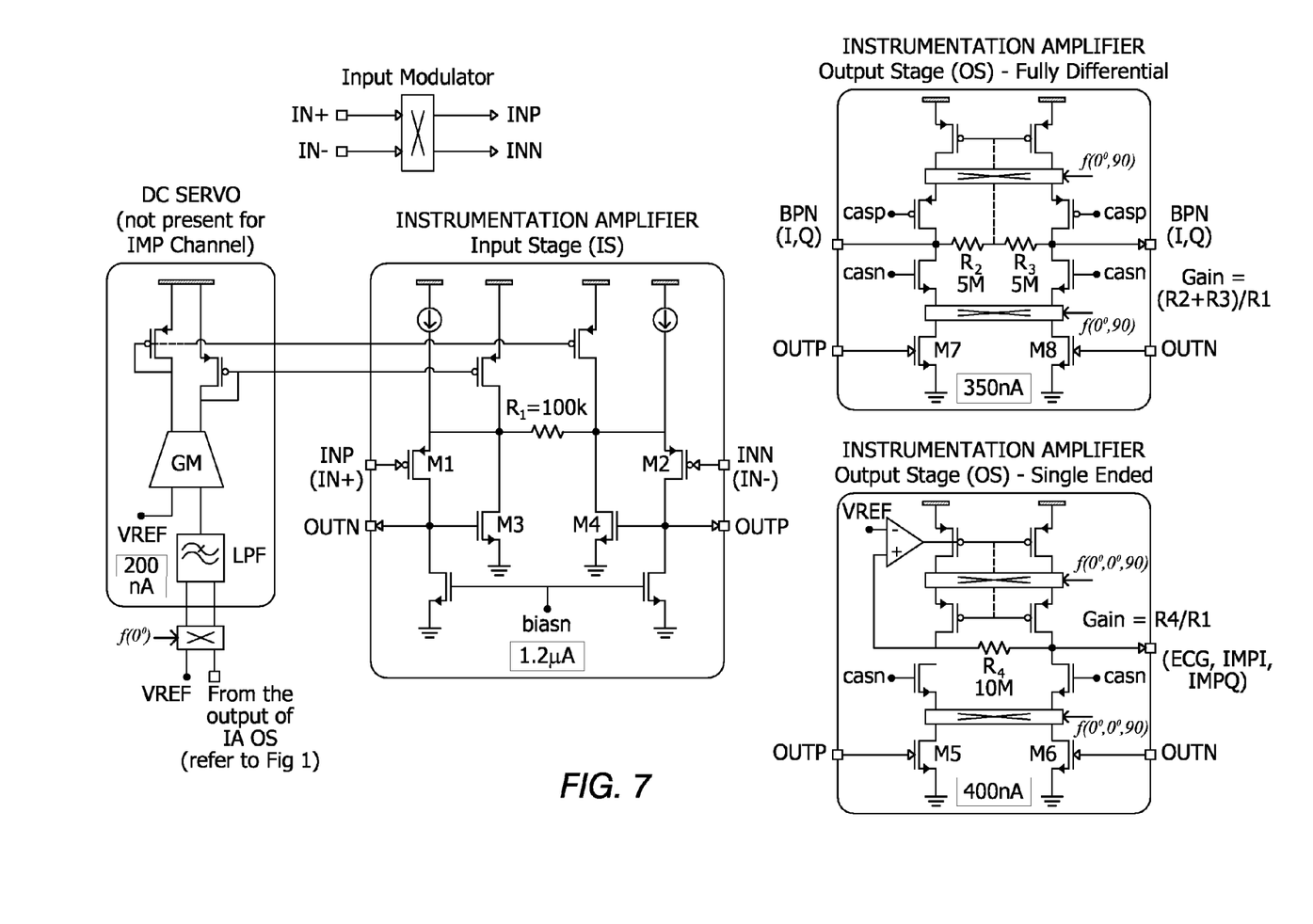
FIG. 7 shows a schematic of a chopper stabilized instrumentation amplifier describing the connectivity of an input stage to multiple output stages, according to one embodiment.

FIG. 7 shows the instrumentation amplifiers architecture used in FIG. 6, comprising two input stages (IS) connected to five output stages (OS). This way of using a single IS with multiple OS for implementing signal paths utilizing the same signal source but implementing different functionalities is enabled by using a current-balancing transconductance stage, similar to Ref. [1], as the IS. The replicas of OS can be connected to OUTP and OUTN in parallel, for instance with different demodulation clock frequencies. Since the demodulators are present at low-impedance nodes of the OS, the different clocking schemes of the OS have minimal affect to each other.

Ref. [2] has shown that tracking power fluctuations of EEG signals in a specific frequency band can be implemented in a power efficient manner. The ASP includes quadrature readout channels similar to [2] with an adjustable demodulation frequency, f+A, to shift the frequency of interest into the bandwidth of the switched-capacitor (SC) low-pass filters (LPF). However, the key difference is the use of a single IA input stage for the quadrature paths and the ECG readout channel 48. This presents an important advantage over [2] in terms of the efficient use of power, where a separate IA is required for each signal path. The input stage of the presented IA consumes 1.2 µA from 2V, while achieving 86 nV/√Hz input referred noise density, whereas each OS consumes 400 nA with negligible noise contribution. This translates into a noise-efficiency-factor (NEF) [4] of 4.7. However, the effective NEF is much lower, since functionality can be increased without the requirement of an additional IA input stage.

Figure 8:
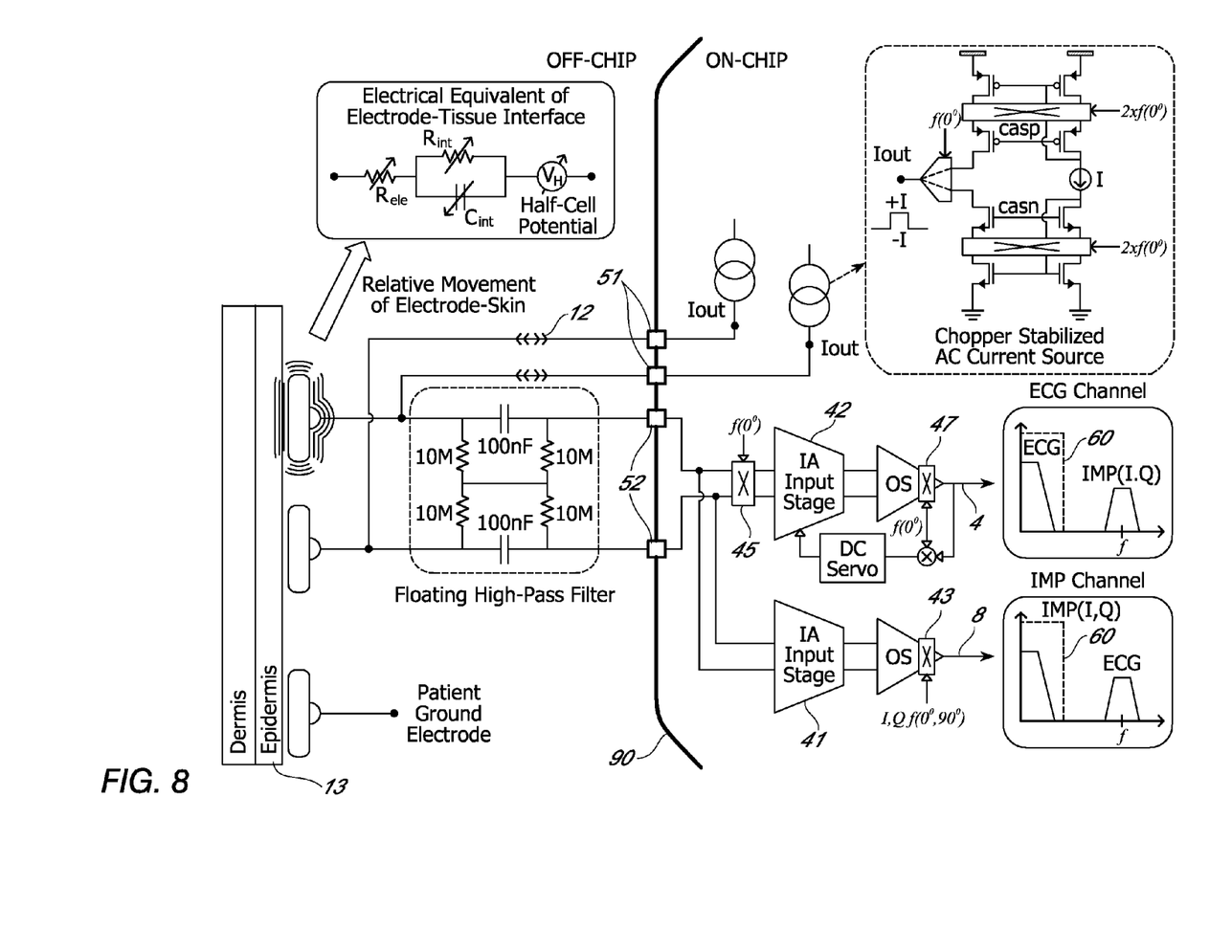
FIG. 8 shows a continuous-time impedance monitoring circuit for monitoring the presence of a motion artifact through impedance measurement.

Ambulatory monitoring of ECG signals can be compromised by motion artifacts. It has been shown that the change of electrode-tissue impedance may be used to monitor the presence of such motion artifacts [5]. However, challenge arises from the requirement of measuring the impedance without affecting the ECG signal in a low-power manner. Referring to FIG. 8, the electrode-tissue interface is stimulated with two AC currents at frequency, f(0°), being equal to 1 kHz. Any DC component of this stimulation current aggravates the motion artifact signal. Hence, the AC current sources incorporate chopper-stabilization at twice the frequency of the AC currents to set the mean value of the stimulation current to zero. The resulting AC voltage over the electrode-tissue interface is only demodulated by the continuous time (CT) impedance monitoring channels. This enables the separation of ECG and impedance signals 4, 8 in the frequency domain by using a low-pass filter 60. Therefore, signal band-power, ECG signal 4, and electrode-tissue impedance 8 can be monitored simultaneously without influencing each other.

Figure 9:
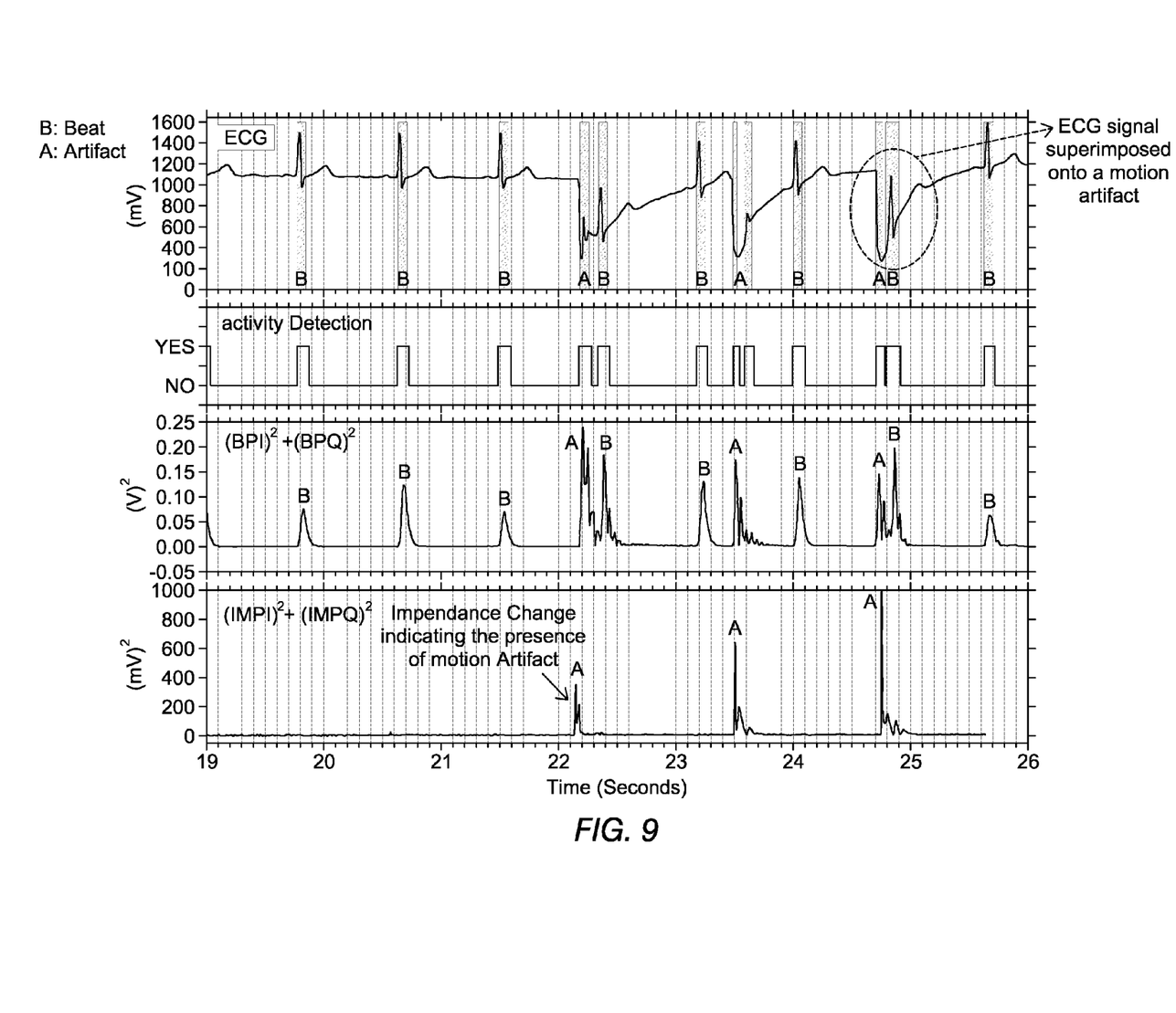
FIG. 9 shows measurement results from the ASP of FIG. 6.

FIG. 9 shows the measured results from the ASP implemented in a standard 0.5 µm CMOS process. The top plot shows the acquired ECG signal. The Activity Detection block successfully detects the high frequency content of QRS complex and the steep edges of the motion artifact signals. Meanwhile, the in-phase (I) and quadrature (Q) band-power extraction channels monitor the signal activity in a selected frequency band (13.7 Hz-18.3 Hz) for the detection of the QRS complex. The measurement (FIG. 9 third graph) shows the sum-of-squares of quadrature channels, clearly indicating a significant power fluctuation during the presence of a QRS complex, as well as, during the presence of motion artifact signals. The incorporated impedance measurement channels (FIG. 9 bottom graph) present a significant change in the electrode-tissue impedance clearly differentiating between a QRS complex (B regions) and motion artifacts (A regions). This shows that the measured impedance can be used as a good indicator of motion artifacts in the measured biopotential signal (FIG. 9 top graph), thereby improving the robustness of signal analysis against motion artifacts.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

Each of the references noted below is incorporated herein by reference in their entirety.

REFERENCES

[1] R. F. Yazicioglu, P. Merken, B. Puers, and C. Van Hoof, "A 200 µW Eight-Channel EEG Acquisition ASIC for Ambulatory EEG Systems," IEEE J. of Solid-State Circuits, vol. 43. no. 12, pp. 3025-3038, December 2008.

[2] A.-T. Avestruz, W. Santa, D. Carlson, R. Jensen, S. Stanslaski, A. Helfenstine, and T. Denison, "A 5 µW/Channel Spectral Analysis IC for Chronic Bidirectional Brain—Machine Interfaces," IEEE J. of Solid-State Circuits, vol. 43. no. 12, pp. 3006-3024, December 2008.

[3] C. C. Enz and G. C. Temes, "Circuit Techniques for Reducing the Effects of Opamp Imperfections," Proc. of IEEE, vol 84, no. 11, pp. 1584-1614, November 1996.

[4] R. R. Harrison and C. Charles, "A Low-Power Low-Noise CMOS Amplifier for Neural Recording Applications," IEEE J. Solid State Circuits, vol. 38, no. 6, pp. 958-965, June 2003.

[5] J. Ottenbacher et. al., "Reliable Motion Artifact Detection for ECG Monitoring Systems with Dry Electrodes" IEEE EMBS Conf., pp. 1695-1698, August 2008.

What is claimed is:

1. An electronic medical device for continuously and simultaneously measuring an impedance signal and a biopotential signal on a biological subject's skin, the device comprising:

input and output electrodes provided for being attached to the biological subject's skin and connected to input and output terminals of the device;

a current source connected to the output terminals configured to generate a predetermined alternating current having a first frequency above a predetermined minimum frequency, the predetermined alternating current being applied to the output electrodes for creating an alternating voltage signal over the input electrodes;

an impedance signal extraction module connected to the input terminals and configured to extract the alternating voltage signal from an input signal which is measured on the input electrodes and to determine the impedance signal from the alternating voltage signal, the impedance signal extraction module comprising a first amplifier connected to the input terminals and configured to amplify the input signal and a demodulation module connected to the first amplifier and configured to demodulate the input signal using a control signal having a frequency equal to the first frequency; and a biopotential signal extraction module connected to the input terminals and configured to extract the biopotential signal from the input signal, wherein the demodulation module comprises first and second demodulation modules using two control signals having a frequency equal to the first frequency but 90° phase shifted with respect to each other, the first and second demodulation modules being configured to extract in parallel a first and a second baseband voltage signal representative of real and imaginary components of the impedance signal.

2. The device according to claim 1, wherein the current source comprises a DC current generator and a first chopper modulator configured to generate the predetermined alternating current, and the first and second demodulation modules are chopper demodulators.

3. The device according to claim 1, wherein the biopotential signal extraction module comprises in sequence a second chopper modulator, a second amplifier, and a third chopper demodulator, the second modulator and the third demodulator being controlled by a clock signal having a second frequency, wherein the second frequency is the same as the first frequency.

4. The device according to claim 1, wherein input and output electrodes are formed by a single set of input/output electrodes connected to a single set of input/output terminals.

5. The device according to claim 1, wherein the current source has a polarity adjustment module configured to adjust the polarity of the modulated current for measuring either a total impedance or an impedance difference.

6. Use of the device according to claim 1 for measuring an ECG or an EEG signal, wherein the impedance signal is used to remove motion artifacts from the biopotential signal.

7. A device for continuously and simultaneously measuring an impedance signal and a biopotential signal on a biological subject's skin, the device comprising:

means for attaching input and output electrodes to the biological subject's skin;

means for applying a predetermined alternating current having a first frequency to the output electrodes for creating an alternating voltage signal over the input electrodes, the first frequency being at least a predetermined minimum frequency;

means for measuring an input signal from the input electrodes, the input signal comprising a biopotential signal and the alternating voltage signal;

means for extracting from the input signal the biopotential signal;

means for extracting from the input signal the alternating voltage signal and determining the impedance signal from the alternating voltage signal by amplifying and demodulating the input signal using a control signal having a frequency equal to the first frequency, the extracting means comprising first and second demodulation modules using two control signals having a frequency equal to the first frequency but 90° phase shifted with respect to each other, the first and second demodulation modules being configured to extract in parallel a first and a second baseband voltage signal representative of real and imaginary components of the impedance signal; and means for determining the impedance signal from the alternating voltage signal.

8. An electronic medical device for continuously and simultaneously measuring an impedance signal and a biopotential signal on a biological subject's skin, the device comprising:

input and output electrodes provided for being attached to the biological subject's skin and connected to input and output terminals of the device;

a current source connected to the output terminals configured to generate a predetermined alternating current having a first frequency above a predetermined minimum frequency, the predetermined alternating current being applied to the output electrodes for creating an alternating voltage signal over the input electrodes;

an impedance signal extraction module connected to the input terminals and configured to extract the alternating voltage signal from an input signal which is measured on the input electrodes and to determine the impedance signal from the alternating voltage signal, the impedance signal extraction module comprising a first amplifier connected to the input terminals and configured to amplify the input signal and a demodulation module connected to the first amplifier and configured to demodulate the input signal using a control signal having a frequency equal to the first frequency; and a biopotential signal extraction module connected to the input terminals and configured to extract the biopotential signal from the input signal, wherein the biopotential signal extraction module comprises in sequence a second chopper modulator, a second amplifier, and a third chopper demodulator, the second modulator and the third demodulator being controlled by a clock signal having a second frequency, wherein the second frequency is the same as the first frequency.

9. The device according to claim 8, wherein input and output electrodes are formed by a single set of input/output electrodes connected to a single set of input/output terminals.

10. The device according to claim 8, wherein the current source has a polarity adjustment module configured to adjust the polarity of the modulated current for measuring either a total impedance or an impedance difference.

11. Use of the device according to claim 8 for measuring an ECG or an EEG signal, wherein the impedance signal is used to remove motion artifacts from the biopotential signal.

* * * * *